US009115374B2

(12) United States Patent
Ihnat et al.

(10) Patent No.: US 9,115,374 B2
(45) Date of Patent: Aug. 25, 2015

(54) SYN3 COMPOSITIONS AND METHODS (75) Inventors: Peter M. Ihnat, Brooklyn, NY (US);
Leonore C. Witchey-Lakshmanan,
Piscataway, NJ (US); Varda Sandweiss,
Forest Hills, NY (US); **Sydney O.
Ugwu**, Chicago, IL (US)

(73) Assignee: MERCK SHARP & DOHME CORP.,
Rahway, NJ (US)

( * ) Notice: Subject to any disclaimer, the term of this patent is extended or adjusted under 35 U.S.C. 154(b) by 0 days.

(21) Appl. No.: 12/838,795

(22) Filed: Jul. 19, 2010

(65) Prior Publication Data

US 2010/0324126 A1 Dec. 23, 2010

Related U.S. Application Data (63) Continuation of application No. 10/329,043, filed on Dec. 20, 2002, now abandoned.

(60) Provisional application No. 60/342,329, filed on Dec. 20, 2001.

(51) Int. Cl.
| | | |
|---|---|---|
| A61K 48/00 | (2006.01) |
| C12Q 1/66 | (2006.01) |
| C12N 15/00 | (2006.01) |
| A01N 63/00 | (2006.01) |
| C12N 15/86 | (2006.01) |
| A61K 9/00 | (2006.01) |
| A61K 9/19 | (2006.01) |
| A61K 31/70 | (2006.01) |
| A61K 31/704 | (2006.01) |
| A61K 47/10 | (2006.01) |
| A61K 47/12 | (2006.01) |
| A61K 47/18 | (2006.01) |
| A61K 47/26 | (2006.01) |
| C07J 41/00 | (2006.01) |

(52) U.S. Cl.
CPC .............. *C12N 15/86* (2013.01); *A61K 9/0019* (2013.01); *A61K 9/19* (2013.01); *A61K 31/70* (2013.01); *A61K 31/704* (2013.01); *A61K 47/10* (2013.01); *A61K 47/12* (2013.01); *A61K 47/18* (2013.01); *A61K 47/26* (2013.01); *A61K 48/0008* (2013.01); *C07J 41/0061* (2013.01); *C12N 2710/10343* (2013.01); *C12N 2710/10351* (2013.01)

(58) Field of Classification Search
None
See application file for complete search history.

(56) References Cited

U.S. PATENT DOCUMENTS

| 5,250,524 A | 10/1993 | Kramer et al. |
| 5,264,618 A | 11/1993 | Felgner et al. |
| 5,789,244 A | 8/1998 | Heidrun et al. |
| 6,013,638 A | 1/2000 | Crystal et al. |
| 6,165,779 A | 12/2000 | Engler et al. |
| 6,312,681 B1 | 11/2001 | Engler et al. |
| 6,392,069 B2 | 5/2002 | Engler et al. |
| 7,002,027 B1 | 2/2006 | Engler et al. |
| 7,105,156 B1 | 9/2006 | Lee et al. |
| 7,534,769 B2 | 5/2009 | Engler et al. |
| 7,538,093 B2 | 5/2009 | Engler et al. |
| 7,691,822 B2 | 4/2010 | Benedict |
| 8,022,044 B2 | 9/2011 | Engler et al. |
| 2001/0006946 A1 | 7/2001 | Engler et al. |
| 2002/0111502 A1 | 8/2002 | Engler et al. |
| 2003/0211598 A1 | 11/2003 | Engler et al. |
| 2004/0014709 A1 | 1/2004 | Engler et al. |
| 2005/0025742 A1 | 2/2005 | Engler et al. |
| 2005/0085427 A1 | 4/2005 | Connor et al. |
| 2005/0287119 A1 | 12/2005 | Benedict |
| 2006/0199782 A1 | 9/2006 | Engler et al. |
| 2010/0266547 A1 | 10/2010 | Benedict |

FOREIGN PATENT DOCUMENTS

| WO | WO 95/10265 A1 | 4/1995 |
| WO | WO 95/29186 A1 | 11/1995 |
| WO | WO 96/10038 A1 | 4/1996 |
| WO | WO 96/10335 A1 | 4/1996 |
| WO | WO 97/25072 A1 | 7/1997 |
| WO | WO 97/40839 A1 | 11/1997 |
| WO | WO 99/02191 A1 | 1/1999 |
| WO | WO 99/45966 A1 | 9/1999 |
| WO | WO 01/03667 A1 | 1/2001 |
| WO | WO 2004/108898 A2 | 12/2004 |

OTHER PUBLICATIONS

Rosser et al 2001, Expert. Rev. Anticancer. Ther 1:531-539.*
Kimura et al 2000, Chem. Pharm. Bull. 48:648-650 Abs. p. 1/1.*
Chemical Reviews 1998, vol. 98, No. (5) pp. 1-2.*
Benedict, William F. et al., *Intravesical Ad-IFNα Causes Marked Regression of Human Bladder Cancer Growing Orthotopically in Nude Mice and Overcomes Resistance to IFN-α Protein*, Mol. Therapy (Sep. 2004) 10(3):525-532.
Connor, R. J. et al., *Identification of polyamides that enhance adenovirus-mediated gene expression in the urothelium*, (2001) Gene Therapy 8:41-48.
Crit Rev Ther Drug Carrier Syst. (1995) 12(4):311-337.
Croyle, Maria A. et al., *Factors That Influence Stability of Recombinant Adenoviral Preparations for Human Gene Therapy*, Pharm. Dev. Technol. (1998) 3(3):373-383.
Croyle, M.A. et al., *Development of formulations that enhance physical stability of viral vectors for gene therapy*, Gene Therapy (2001) 8:1281-1290.
European Search Report mailed on Sep. 3, 2009, for EP Application No. 09008139.9, 5 pages.
Gardli et al., *Med. Sci. Monit* (2005) 11:RA110-121.

(Continued)

Primary Examiner — Christopher M Babic
Assistant Examiner — Kelaginamane T Hiriyanna
(74) Attorney, Agent, or Firm — Kilpatrick Townsend & Stockton LLP (57) ABSTRACT Disclosed are aqueous and lyophilized formulations containing SYN3 and methods of their use for treating bladder cancer.

7 Claims, 2 Drawing Sheets (56) References Cited

OTHER PUBLICATIONS

Goncalves, *Bioessays* (2005) 27:506-517.

Horton, Holly M. et al., *Antitumor Effects of Interferon-ω: In Vivo Therapy of Human Tumor Xenografts*, Cancer Res. (Aug. 15, 1999) 59:4064-4068.

Kukowska-Latallo, J. et al., "Efficient transfer of genetic material into mammalian cells using Starburst polyamidoamine dendrimers," *Proc. Natl. Acad. Sci. USA* (May 1996) 93:4897-4902.

Verman and Weitzman, *Ann. Rev. Biochem* (2005) 74:711-738.

Walker, S. et al., "Cationic facial amphiphiles: A promising class of transfection agents," *Proc. Natl. Acad. Sci. USA* (Feb. 1996) 93:1585-1590.

Yamashita, et al., *Cancer Gene Therapy*, (2002) 9:681-686.

Zhou et al., *Cancer Gene Therapy* (2002) 9:681-686.

Supplementary European Search Report mailed on May 27, 2010, for EP Application No. 02805671.1 filed on Dec. 20, 2002, 3 pages.

Ahmed et al., "Interferon α2b gene delivery using adenoviral vector causes inhibition of tumor growth in xenograft models from a variety of cancers," Cancer Gene Therapy, Oct. 2001, 8:788-795.

Li et al., "Introduction of wild-type p53 gene downregulates the expression of H-ras gen and suppresses the grown of bladder cancer cells," Urol. Res., 1995, 23(5):311-314.

Seigne et al., "Rationale and development of retinoblastoma tumor suppressor gene therapy for bladder cancer," Journal of Urology, 1996, 155(5 suppl.):320A.

Talsma, H. et al., "Stabilization of gene delivery systems by freeze-drying," *Int. J. Pharm.*, Nov. 28, 1997, 157(2):233-238.

Werthman, et al., "Adenoviral-P53 Gene Transfer to Orthotopic and Peritoneal Murine Bladder Cancer," *J. Urol.*, Feb. 1996, 155(2):753-756.

Albers et al. "Complexation of Steroid Hormones with Cyclodextrin Derivatives: Substituent Effects of the Guest Molecule on Solubility and Stability in Aqueous Solution," Journal of Pharmaceutical Sciences, Aug. 1992, vol. 81, No. 8, pp. 756-761.

Anderson et al., "Brain-Enhanced Delivery of Testosterone Using a Chemical Delivery System Complexed with 2-Hydroxypropyl-β-Cyclodextrin," Drug Design and Delivery, 1988, vol. 2, pp. 287-298.

Brewster et al., "Improved Delivery through Biological Membranes XXXI: Solubilization and Stabilization of an Estradiol Chemical Delivery System by Modified β-Cyclodextrins," Journal of Pharmaceutical Sciences, 1988, vol. 77, No. 11, pp. 981-985.

Muller et al., "Effect of Hydrotropic Substances on the Complexation of Sparingly Soluble Drugs with Cyclodextrin Derivatives and the Influence of Cyclodextrin Complexation on the Pharmacokinetics of the Drugs," Journal of Pharmaceutical Sciences, Jun. 1991, vol. 80(6), pp. 599-604.

\* cited by examiner

SYN3 COMPOSITIONS AND METHODS

CROSS-REFERENCES TO RELATED APPLICATIONS

This application is a continuation of U.S. Patent Application No. 10/329,043, filed Dec. 20, 2002 now abandoned, which claims priority to U.S. Patent Application No. 60/342,329, filed Dec. 20, 2001, the disclosure of each of which is hereby incorporated by reference in its entirety for all purposes.

FIELD OF INVENTION

The present invention is directed to compositions for treating cancer by gene therapy using a therapeutic gene, such as a tumor suppressor gene delivered by a gene delivery system, such as a recombinant viral vector delivery system, in combination with a transduction enhancing agent. In particular, this invention relates to the delivery of a tumor suppressor gene (e.g., p53 or retinoblastoma (RB)) to cancerous epithelial tissues and organs, such as the bladder, using a recombinant adenoviral vector delivery system formulated in a stabilized buffer in combination with a transduction enhancing agent, such as SYN3.

BACKGROUND OF THE INVENTION

Epithelial Cancer is an insidious disease. For instance, one type of epithelial cancer, carcinoma of the bladder, represents a significant source of morbidity and mortality. Bladder cancer reportedly ranks 10th in males and 12th in females in cancer related mortality. Therapies available for the treatment of bladder cancer include adjuvant chemotherapy or immunotherapy, transurethral resection of superficial disease, radical cystectomy or radiotherapy which is often combined with systemic chemotherapy. Despite these therapeutic options, overall survival has not changed appreciably. Thus, new therapeutic modalities must be developed for the treatment of bladder cancer.

Gene therapy strategies have been reportedly developed as an alternative therapeutic approach. Distinct approaches have been developed to treat neoplasms based on gene transfer methods. Methods have been reportedly developed to correct specific lesions at defined genetic loci which give rise to neoplastic transformation and progression. Overexpression of dominant oncogenes can be addressed using techniques to inhibit the transforming gene or gene product. It has been reported that loss of tumor suppressor gene function may be approached using methods to reconstitute wild-type tumor suppressor gene. Besides these methods to achieve mutation compensation, genetic techniques have been reportedly developed to specifically and selectively eradicate tumor cells. These approaches of molecular chemotherapy reportedly rely on specific expression of toxin genes in neoplastic cells. Finally, gene transfer methods have been reportedly used to achieve antitumor immunization. These methods of genetic immunopotentiation reportedly use techniques of genetic immunoregulation to enhance immune recognition of tumors. Consequently, a variety of distinct approaches reportedly have been developed to accomplish gene therapy of cancer.

A high incidence of mutations has reportedly been observed in tumor suppressor genes, such as p53 and RB, in the case of carcinoma of the bladder. For such genetic lesions of tumor suppressor genes, reversion of the neoplastic phenotype can be demonstrated with replacement of the corresponding wild-type tumor suppressor gene.

In vitro studies using cell lines derived from human bladder tissues have reportedly demonstrated efficient transgene expression following infection with recombinant adenovirus. Experiments in vivo reportedly have also shown adenovirus transgene expression in the urinary bladder of rodents after intravesical delivery. In vitro experiments with wild-type adenovirus demonstrate that virus attachment and internalization is not influenced by benzyl alcohol, but do reportedly demonstrate an enhanced uncoating of the virion. In vivo efforts with agents (e.g. acetone, DMSO, prolamine sulfate) can reportedly break down the protective "mucin" layer that protects the bladder epithelium from bacteria, viruses and other pathogens.

U.S. Pat. No. 5,789,244 claims a composition comprising a viral vector in which a nucleotide sequence encoding a transgene has been inserted, wherein the viral vector is formulated in a buffer comprising ethanol in a concentration range of about 1% to 50% (v/v). U.S. Pat. No. 5,837,520 claims a method for purification of an intact viral particle from a cell lysate comprising treating the cell lysate which contains the intact viral particle with an enzymatic agent that selectively degrades both unencapsulated DNA and RNA; chromatographing the treated lysate from the first step on a first resin; and chromatographing the eluant from the second step on a second resin; wherein one resin is an anion exchange resin and the other is an immobilized metal ion affinity resin. U.S. Pat. No. 5,932,210 describes a composition comprising a recombinant adenovirus expression vector and a pharmaceutically acceptable carrier, the vector comprising: (a) an insert of exogenous DNA comprising a gene encoding a foreign protein; and (b) adenovirus DNA in which all of the coding sequences of E1a, E1b, and protein IX, and at least part of E3 have been deleted. U.S. Pat. No. 6,165,779 discloses a composition comprising a recombinant virus vector formulated in a buffer comprising a detergent. U.S. Pat. No. 6,210,939 claims a recombinant adenovirus expression vector comprising (a) an insert of exogenous DNA comprising a gene encoding a foreign protein and (b) adenovirus DNA which has sustained a deletion beginning at nucleotide 357 and ending at nucleotide 4020 to 4050. Finally, U.S. Pat. No. 6,312,681 discloses a method for delivering an adenoviral vector which comprises a transgene to a cancer cell in the epithelial membrane of a bladder, the method comprising administering to the epithelial membrane the adenoviral vector and between 1% and 50% (v/v) ethanol, wherein the adenoviral vector infects the cell and the transgene is expressed in infected cells. All of these references are hereby incorporated by reference thereto in their entirety.

Notwithstanding the foregoing, there exists a need for formulations for therapeutic use that improve the efficiency of the transgene delivery. Vectors that are unstable present difficulty in administering the desired therapeutic agent to the patient. Because of in vivo instability, there is a need for vector stabilization such that there is an increase in the transduction of the therapeutic agent that is to be administered.

SUMMARY OF THE INVENTION

Accordingly, in one aspect, the present invention provides a pharmaceutical composition comprising SYN3 in combination with a pharmaceutically acceptable carrier.

A further aspect of the invention is a pharmaceutical composition comprising SYN3 in combination with a pharmaceutically acceptable nonaqueous carrier.

A further aspect of the invention is a pharmaceutical composition comprising SYN3 in combination with a pharmaceutically acceptable aqueous carrier.

A further aspect of the invention is a pharmaceutical composition comprising SYN3 in combination with a pharmaceutically acceptable carrier and at least one pharmaceutically acceptable solubilizer.

A further aspect of the invention is a pharmaceutical composition comprising SYN3 in combination with a pharmaceutically acceptable nonaqueous carrier and at least one pharmaceutically acceptable solubilizer.

A further aspect of the invention is a pharmaceutical composition comprising SYN3 in combination with a pharmaceutically acceptable aqueous carrier and at least one pharmaceutically acceptable solubilizer.

A further aspect of the invention is a lyophilized pharmaceutical composition comprising SYN3 in combination with a pharmaceutically acceptable carrier, at least one pharmaceutically acceptable solubilizer and a at least one pharmaceutically acceptable bulking agent.

A further aspect of the invention is a pharmaceutical composition comprising SYN3 in combination with a pharmaceutically acceptable aqueous carrier, at least one pharmaceutically acceptable solubilizer, and at least one pharmaceutically acceptable bulking agent.

A further aspect of the invention is a pharmaceutical composition comprising SYN3 in combination with a pharmaceutically acceptable aqueous carrier, at least one pharmaceutically acceptable solubilizer, at least one pharmaceutically acceptable bulking agent and at least one pharmaceutically acceptable buffering agent.

A further aspect of the invention is a pharmaceutical composition comprising SYN3 in combination with a pharmaceutically acceptable carrier and an expression vector comprising a foreign DNA sequence inserted into the vector.

A further aspect of the invention is a pharmaceutical composition comprising SYN3 in combination with a pharmaceutically acceptable nonaqueous carrier and an expression vector comprising a foreign DNA sequence inserted into the vector.

A further aspect of the invention is a pharmaceutical composition comprising SYN3 in combination with a pharmaceutically acceptable aqueous carrier and an expression vector comprising a foreign DNA sequence inserted into the vector.

A further aspect of the invention is a pharmaceutical composition comprising SYN3 in combination with a pharmaceutically acceptable carrier, an expression vector comprising a foreign DNA sequence inserted into the vector and at least one pharmaceutically acceptable solubilizer.

A further aspect of the invention is a pharmaceutical composition comprising SYN3 in combination with a pharmaceutically acceptable nonaqueous carrier, an expression vector comprising a foreign DNA sequence inserted into the vector and at least one pharmaceutically acceptable solubilizer.

A further aspect of the invention is a pharmaceutical composition comprising SYN3 in combination with a pharmaceutically acceptable aqueous carrier, an expression vector comprising a foreign DNA sequence inserted into the vector and at least one pharmaceutically acceptable solubilizer.

A further aspect of the invention is a pharmaceutical composition comprising SYN3 in combination with a pharmaceutically acceptable aqueous carrier, an expression vector comprising a foreign DNA sequence inserted into the vector, at least one pharmaceutically acceptable solubilizer, and at least one pharmaceutically acceptable bulking agent.

A further aspect of the invention is a pharmaceutical composition comprising SYN3 in combination with a pharmaceutically acceptable aqueous carrier, an expression vector comprising a foreign DNA sequence inserted into the vector, at least one pharmaceutically acceptable solubilizer, at least one pharmaceutically acceptable bulking agent and at least one pharmaceutically acceptable buffering agent.

A further aspect of the invention is a use of SYN3 in the preparation of a medicament for the treatment of bladder cancer.

A further aspect of the invention is a method of treating a disease in a mammal comprising administering a therapeutically effective amount of a pharmaceutical composition comprising SYN3 in combination with a pharmaceutically acceptable carrier.

These and other aspects, objects and advantages will become more apparent when read with the accompanied detailed description which follows.

DETAILED DESCRIPTION OF THE INVENTION

Accordingly, one aspect of the invention is that a unique surfactant-like molecule SYN3 is formulated with excipients to maintain solubility and stability as well as compatibility with the adenovirus.

A further aspect of the invention is that the SYN3 formulations are nontoxic to tissues, e.g., the bladder with which it comes in contact at therapeutic levels. Indeed, surfactants which act as permeation enhancers often produce some toxicity due to membrane irritation. The use of SYN3 thus provides this further benefit of avoiding this toxicity. Connor, et al., *Gene Therapy*, Vol. 8, pp. 41-48 (2001).

A further aspect of the invention is that the stability of the vector is unaffected by combination with the SYN3. Often, surfactant levels required to improved transduction may impart instability to the vector. Combination of the adenovirus and SYN3 preparations produces a more potent admixture compared with adenovirus.

Figure 1:
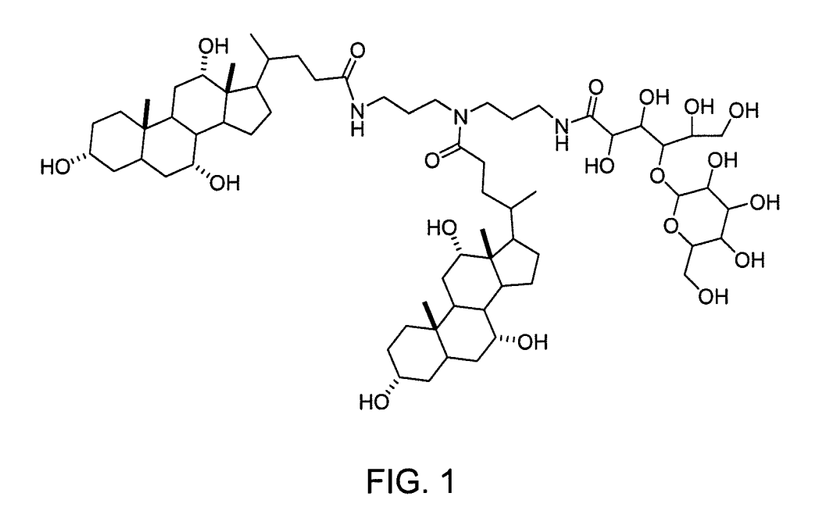
FIG. 1 illustrates a chemical structural formula of SYN3.

Buffered and lyophilized aqueous formulations as well as nonaqueous solution formulations of SYN3 were produced. SYN3, is (N—(3-cholamidopropyl)—N—(3-lactobionamidopropyl))-cholamide (FIG. 1). As will be apparent to those of skill in the art, SYN3 exists in various optical, tautomeric, stereoisomeric and isomeric forms. FIG. 1 illustrates a preferred isomer. However, the compositions of the present invention encompass all such forms in any percentage or racemic mixture thereof.

SYN3 is a surfactant-like molecule that enhances transduction of recombinant adenovirus/therapeutic gene vectors for treatment of epithelial tissue and tumors, or, more specifically, in bladder tumors. SYN3 can be present in a concentration of from about 0.001mg/ml to about 150mg/ml.

The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53gene, the APC gene, the DPC-4gene, the BRCA-1gene, the BRCA-2 gene, the WT-1 gene, the retinoblastoma gene (Lee, et al., Nature, 329:642 (1987)), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3. (Cheng, et al., *Proc. Nat. Acad. Sci.*, 95:3042-3047 (1998)), the MTS 1 gene, the CDK4 gene, the NF-1 gene, the NF2 gene, and the VHL gene.

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilitate immune recognition, the antigenic gene may be fused to the MHC class I antigen.

The term "cytotoxic gene" refers to nucleotide sequence, the expression of which in a cell produces a toxic effect. Examples of such cytotoxic genes include nucleotide sequences encoding pseudomonas exotoxin, ricin toxin, diptheria toxin, and the like.

The term "cytostatic gene" refers to nucleotide sequence, the expression of which in a cell produces an arrest in the cell cycle. Examples of such cytostatic genes include p21, the retinoblastoma gene, the E2F-Rb gene, genes encoding cyclin dependent kinase inhibitors such as P16, p15, p18 and p19, the growth arrest specific homeobox (GAX) gene as described in Branellec, et al. (PCT Publication WO97/16459 published May 9, 1997 and PCT Publication WO96/30385 published Oct. 3, 1996).

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the alpha, beta and gamma subtypes especially interferon α-2b and fusions such as interferon α-2α-1.

The term "chemokine gene" refers to a nucleotide sequence, the expression of which in a cell produces a cytokine. The term chemokine refers to a group of structurally related low-molecular cytokines weight factors secreted by cells are structurally related having mitogenic, chemotactic or inflammatory activities. They are primarily cationic proteins of 70 to 100 amino acid residues that share four conserved cysteine. These proteins can be sorted into two groups based on the spacing of the two amino-terminal cysteines. In the first group, the two cysteines are separated by a single residue (C-x-C), while in the second group, they are adjacent (C—C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and I (AMCF-I and -II), pre-B cell growth stimulating factor (PBSF), and IP10. Examples of members of the 'C—C' group include, but are not limited to, monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 alpha (MIP-1-alpha), macrophage inflammatory protein 1 beta (MIP-1-beta), macrophage inflammatory protein 1 gamma (MIP-1-gamma), macrophage inflammatory protein 3 alpha (MIP-3-alpha, macrophage inflammatory protein 3 beta (MIP-3-beta), chemokine (ELC), macrophage inflammatory protein 4 (MIP-4), macrophage inflammatory protein 5 (MIP-5), LD78 beta, RANTES, SIS-epsilon (p500), thymus and activation-regulated chemokine (TARC), eotaxin, 1-309, human protein HCC-1/NCC-2, human protein HCC-3, mouse protein C10.

The term "pharmaceutical protein gene" refers to nucleotide sequence, the expression of which results in the production of protein have pharmaceutically effect in the target cell. Examples of such pharmaceutical genes include the proinsulin gene and analogs (as described in PCT International Patent Application No. WO98/31397, growth hormone gene, dopamine, serotonin, epidermal growth factor, GABA, ACTH, NGF, VEGF (to increase blood perfusion to target tissue, induce angiogenesis, PCT publication WO98/32859 published Jul. 30, 1998), thrombospondin etc.

The term "pro-apoptotic gene" refers to a nucleotide sequence, the expression thereof results in the programmed cell death of the cell. Examples of pro-apoptotic genes include p53, adenovirus E3-11.6K, the adenovirus E4 or f4 gene, p53 pathway genes, and genes encoding the caspases.

The term "pro-drug activating genes" refers to nucleotide sequences, the expression of which, results in the production of protein capable of converting a nontherapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5 fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS (USA)(1998) 95:8795-8800), endostatin.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention as described in Wahl, et al., *Nat. Cell Biol.*, 3(12):E277-86 (2001), deletions such as the deltal3-19 amino acids to eliminate the calpain consensus cleavage site, modifications to the oligomerization domains (as described in Bracco, et al. PCT published application WO97/0492 or U.S. Pat. No. 5,573, 925).

It will be readily apparent to those of skill in the art that the above therapeutic genes may be secreted into the media or localized to particular intracellular locations by inclusion of a targeting moiety such as a signal peptide or nuclear localization signal (NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding noninfected cells to a diameter of approximately 16 cells wide. This system is particularly useful in conjunction with transcriptionally active proteins (e.g. p53) as the fusion proteins are efficiently transported to the nuclei of the surrounding cells. See, e.g. Elliott, G. & O'Hare, *P. Cell.*, 88:223-233 (1997); Marshall, A. & Castellino, A. Research News Briefs., *Nature Biotechnology*, 15:205 (1997); O'Hare, et al. PCT publication WO97/05265 published Feb. 13, 1997. A similar targeting moiety derived from the HIV Tat protein is also described in Vives, et al., *J. Biol. Chem.*, 272:16010-16017 (1997).

As used herein, "a gene delivery system" refers to any means of delivery of a therapeutic gene to a particular epithelial tissue or organ including, for example, recombinant viral vectors and nonviral vector systems. Examples of nonvector systems include, but are not limited to, any lipid-based, lipid encapsulated DNA or cationic lipid/DNA complexes. Examples of recombinant viral vectors include, but are not limited to, herpes virus, retrovirus, vaccinia virus, adenovirus, and adenoassociated viruses.

"Recombinant" refers to nucleic acids and protein encoded by them wherein the nucleic acids are constructed by methods of recombinant DNA technology, also termed "genetic engineering". A preferred recombinant viral vector is the adenoviral vector delivery system which has a deletion of the protein IX gene. See International patent Application WO 95/11984, which is herein incorporated by reference in its entirety. The recombinant vector delivery system comprising a therapeutic gene, such as a tumor suppressor gene, is formulated in a buffer that stabilizes the vector and is combined with a delivery enhancing agent that is compatible with the vector.

A "delivery-enhancing agent" refers to any agent which enhances delivery of a therapeutic gene, such as a tumor suppressor gene to a cancerous tissue or organ. Such enhanced delivery may be achieved by various mechanisms. One such mechanism may involve the disruption of the protective glycosaminoglycan layer on the epithelial surface of the bladder.

Examples of such delivery-enhancing agents are detergents, alcohols, glycols, surfactants, bile salts, heparin antagonists, cyclooxygenase inhibitors, hypertonic salt solutions, and acetates. Alcohols include, for example, the aliphatic alcohols such as ethanol, N-propanol, isopropanol, butyl alcohol, acetyl alcohol. Glycols include, for example, glycerol, propyleneglycol, polyethyleneglycol, and thioglycerol. Acetates such as acetic acid, gluconol acetate, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 20, polyoxyethylene ethers, and polyglycol ether surfactants. Bile salts such as taurocholate, sodium tauro-deoxycholate, deoxycholate, chenodesoxycholate, glycocholic acid, glycochenodeoxycholic acid and other astringents like silver nitrate may be used. Heparin-antagonists like quaternary amines such as protamine sulfate may also be used. Cyclooxygenase inhibitors such as sodium salicylate, salicylic acid, and nonsteroidal antiinflammatory drug (NSAIDS) like indomethacin, naproxen, diclofenac may be used.

The term "enhanced" describes the increased delivery of the therapeutic gene, such as a tumor suppressor gene, to the cancerous tissue or organ. Increased delivery of a therapeutic gene, such as a tumor suppressor gene, can be measured by various means, for example by measuring expression of the tumor suppressor gene compared to expression levels when the tumor suppressor gene is delivery in an adenoviral vector delivery system in a buffer lacking the delivery-enhancing agent. Examples of therapeutic genes are tumor suppressor genes and the suicide gene thymidine kinase. Examples of tumor suppressor genes include, but are not limited to, p53, the retinoblastoma gene, either full length, such as p110B, or fragments thereof such as p94RB or p56RB, RB56, a functional variant of Rb gene, a functional variant of the p53 gene, and p16. Other therapeutic genes include but are not limited to CFTR, genes encoding cytokines (such as the interferons alpha, beta, gamma, delta, interleukins (e.g., IL-4, IL-10, IL-2), GM-CSF, and any other genes encoding proteins which have therapeutic potential in the treatment of noncancerous diseases of the bladder such as cystitis. In some embodiments of the invention, the therapeutic gene encodes antisense RNA.

In some embodiments, the compositions of the invention comprise a therapeutically effective amount of a therapeutic gene, such as a tumor suppressor gene, contained in a recombinant viral vector delivery system in a buffer comprising a delivery-enhancing agent. "Therapeutically effective" as used herein refers to the prevention of, reduction of, or curing of symptoms associated with a disease state.

Therapeutically effective amounts of the pharmaceutical composition comprising a therapeutic gene, such as p53, or the retinoblastoma tumor suppressor gene, in a recombinant viral vector delivery system formulated in a buffer comprising a delivery-enhancing agent will be administered in accord with the teaching of this invention. For example, therapeutically effective amounts of the p53 tumor suppressor gene in the recombinant adenoviral vector delivery system formulated in a buffer containing a delivery-enhancing agent are in the range of about $1 \times 10^8$ particles/ml to $2 \times 10^{12}$ particles/ml, more typically about $1 \times 10^8$ particles/ml to $9 \times 10^{11}$ particles/ml, most typically $1 \times 10^{10}$ particles/ml to $9 \times 10^{11}$ particles/ml.

P53, also known as ACN53, is a recombinant adenovirus type 5 encoding wild-type p53 tumor suppressor protein, and is described in, for example, PCT patent application WO95/11984. In one aspect of the invention, the formulated SYN3 is combined with p53 injection and the admixture is instilled into the bladder. This preparation is intended to treat epithelial carcinomas. Preferably, p53 will be present in an amount of about 5 to about $8 \times 10^{13}$ particles.

Detergents for use within the scope of the present invention include, for example, anionic, cationic, zwitterionic, and nonionic detergents. Exemplary detergents include, for example, but are not limited to taurocholate, deoxycholate, taurodeoxycholate, cetylpyridium, benalkonium chloride, ZWITTERGENT 3-14 detergent, CHAPS (3-[(3-Cholamidopropyl)dimethylammoniol]-1-propanesulfonate hydrate, available from Aldrich, Big CHAP, Deoxy Big CHAP, TRITON-X-100 detergent available from Union Carbide, C12E8, Octyl-B-D-Glucopyranoside, PLURONIC-F64, PLURONIC-F68, PLURONIC-F69 detergents available form BASF, TWEEN20 detergent, and TWEEN80 detergent available from ICI.

In an embodiment, the delivery-enhancing agent is included in the buffer in which the recombinant adenoviral vector delivery system is formulated. The delivery-enhancing agent may be administered prior to the recombinant virus or concomitant with the virus. In some embodiments, the delivery-enhancing agent is provided with the virus by mixing a virus preparation with a delivery-enhancing agent formulation just prior to administration to the patient. In other embodiments, the delivery-enhancing agent and virus are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition may be administered over time in the range of about 5 minutes to 3 hours, preferably about 10 minutes to 120 minutes, and preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and preferably about 1 minute to 5 minutes prior to administration of the adenoviral vector delivery system containing the tumor suppressor gene.

Solvents that may be used for the formulations of the present invention include, for example, aqueous solvents such as water for injection, and/or nonaqueous solvents, such as DMSO and N,N-Dimethyylacetamide, also known as DMA, and co-solvent mixtures, e.g., glycerol and water, as prepared preferably in accordance with USP standards.

The formulations preferably contain polysorbates, or polyoxyethylene sorbitan esters, a class of nonionic surfactants that included, e.g., polysorbate 80 and polysorbate 20, amongst others, Pluronics, or polyethylenepolypropylene glycol block copolymers, a class of nonionic surfactants, that include e.g. Pluronic L68 and L92, amongst others, and hydroxypropyl-beta-cyclodextrin, a polysubstituted hydroxyalkyl-beta-cyclodextrin, which is a class of nonionic complexing agents, that include, e.g., HPβCD and BigCHAP. Preferred are HPβCD, BigCHAP, Polysorbate 80, Polysorbate 20, Pluronic L64, and Pluronic L92 as solubilizing agents. The solubilizers can be used, for example, either individually or in combinations. The concentrations of the solubilizing agents are set forth below. HPβCD can be present in a concentration of about 50 to 500 mg/ml, BigCHAP can be present in a concentration of about 20 to about 360 mg/ml, Polysorbate 80 can be present in a concentration of about 1 to 36 mg/ml, the Pluronics can be present in concentrations of about 1 to about 150 mg/ml, and the other ingredients may be present in concentrations as set forth below.

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 0.01% to 50% (w/v), preferably 10% to 40% (w/v), preferably 14% to 19% (w/v), and preferably 0.01% to 30% (w/v). Preferably, the detergent concentration will be about 1% to 12% (w/v) in the formulation prior to admixture, and preferably 0.1% (w/v) of the formulation when in admixture. Preferably, the detergent concentration in the final formulation administered to the patient is about 0.5-2 times the critical micellization concentration (CMC). The CMC is equal to 0.001 mg/ml in the recombinant adenovirus formulation.

The lyophilized formulations of SYN3 preferably contain a citrate buffering system. More preferably, the citrate buffering system can comprise at least one citric buffer, such as citric acid monohydrate USP or sodium citrate dihydrate USP. More preferably, the citrate buffering system comprises a combination of citric acid monohydrate USP and sodium citrate dihydrate USP. When used in combination, the amount of citric acid monohydrate USP can be present in a concentration of about 0.005 to about 2 mg/ml, more preferably 0.016 to about 1.35 mg/ml, preferably 0.016 to about 0.72 mg/ml, preferably about 0.005 to about 1.35, and the sodium citrate dihydrate USP can be present in a concentration of about 0.02 to about 5.37 mg/ml, preferably 0.05 to 3.00 mg/ml, preferably 0.05 to 2.31 mg/ml. Other suitable buffering systems that are suitable include, for example, phosphate, glycine, either in place of the citrate buffering system or in combination therewith, and varying combinations of all of the above.

The buffering system will provide a pH of the lyophilized formulation such that there is improved stability. Preferably, the pH will be in a range of about 5 to about 6. The admixture aqueous formulations of SYN3 are preferably buffered at about a pH of about 7 to about 8.5, preferably about 7.4, and SYN3 remains stable in the dehydrated powder for at least 3 months at 40° C.

The lyophilized formulations preferably contain glycine or mannitol as freeze-drying bulking agents. Other suitable freeze-drying bulking agents that may be used include, for example, lactose, recombinant gelatin, and methylcellulose. The freeze drying-bulking agent may be present in a concentration of from about 5 to 100 mg/ml when the agent is mannitol, and about 10 to 200 mg/ml when the agent is glycine.

The lyophilized formulations preferably contain ascorbic acid as an antioxidant. Other suitable antioxidants that may be used include, for example, citric acid. When ascorbic acids is the antioxidant, it may be present in a concentration of about 0.001 to about 0.6 mg/ml.

The compositions of this invention may additionally include, for example, a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene A physiologically acceptable compound can include, for example, carbohydrates, such as glucose, sucrose or dextrans, Hydroxypropyl-β-Cyclodextrin, antioxidants, such as ascorbic acid or glutathione, chelating agents, low molecular weight proteins or other stabilizers or excipients.

Other physiologically acceptable compounds include, for example, wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physiochemical characteristics of the recombinant adenoviral vector delivery system and the particular tumor suppressor gene contained therein. Examples of carriers, stabilizers or adjuvants can be found in Gennaro, Remington's: *The Science and Practice of Pharmacy,* 19th Ed. (Mack Publishing. Co., Easton, Pa. 1995), incorporated herein by reference.

The recombinant viral vector delivery system comprising a therapeutic gene formulated in a buffer comprising a delivery-enhancing agent may be delivered to any cancerous tissue or organ using any delivery method known to the ordinarily skilled artisan for example, intratumoral or intravesical administration. Cancerous tissues and organs include, for example, any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

The delivery-enhancing agents of the invention can also be used to formulate other pharmaceutical agents, such as proteins, nucleic acids, antisense RNA, small molecules, etc., for administration to any tissue or organ having an epithelial membrane.

Administration of Formulations

In some embodiments, the delivery-enhancing agent is included in the buffer in which an expression vector is formulated. The delivery-enhancing agent can be administered prior to the expression vector or concomitant with the expression vector. In some embodiments, the delivery-enhancing agent is provided with the expression vector by mixing an expression vector with a delivery-enhancing agent formulation just prior to administration to the patient. In other embodiments, the delivery-enhancing agent and the expression vector are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition can be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The expression vector formulated in a buffer comprising a delivery-enhancing agent can be delivered to any tissue or organ, including neoplastic tissues such as cancer tissue, using any delivery method known to the ordinarily skilled artisan for example, intratumoral or intravesical administration. Tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

In some embodiments of the invention, an expression vector is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701. Such formulations are especially useful for the treatment of cancers of the mouth, head and neck cancers (e.g., cancers of the tracheobronchial epithelium) skin cancers (e.g., melanoma, basal and squamous cell carcinomas), cancers of the intestinal mucosa, vaginal mucosa, and cervical cancer.

In some embodiments of the invention, a therapeutic agent is formulated in ophthalmic formulations for administration to the eye. Such formulations are useful in the delivery of the retinoblastoma (RB) gene to the eye, optionally in conjunction with the delivery of p53.

Methods of Treatment

The composition of the invention are typically administered to enhance transfer of gene to a cell. The cell can be provided as part of a tissue, such as an epithelial membrane, or as an isolated cell, such as in tissue culture. The cell can be provided in vivo, ex vivo, or in vitro.

The compositions can be introduced into the tissue of interest in vivo or ex vivo by a variety of methods. In some embodiments of the invention, the modulating agent is introduced to cells by such methods as microinjection, calcium phosphate precipitation, liposome fusion, or biolistics. In further embodiments, the therapeutic agent is taken up directly by the tissue of interest.

In some embodiments of the invention, the compositions of the invention are administered ex vivo to cells or tissues explanted from a patient, then returned to the patient. Examples of ex vivo administration of therapeutic gene constructs include Arteaga et al., Cancer Research 56(5):1098-1103 (1996); Nolta et al., Proc Natl. Acad. Sci. USA 93(6): 2414-9 (1996); Koc et al., Seminars in Oncology 23 (1):46-65 (1996); Raper et al., Annals of Surgery 223(2):116-26 (1996); Dalesandro et al., J. Thorac. Cardi. Surg., 11(2):416-22 (1996); and Makarov et al., Proc. Natl. Acad. Sci. USA 93(1): 402-6 (1996).

EXAMPLES

The following examples will further illustrate the present invention.

Example 1

The following table represents ranges of the ingredients for nonaqueous liquid formulations of the present invention. Prior to administration (for bladder cancer), the SYN3 solution is combined with the recombinant adenovirus preparation in a 1:50 v/v ratio to form an admixture that is administered to the patient.

|  | Range of Ingredient Concentrations | | | |
| --- | --- | --- | --- | --- |
| Ingredient | mg/ml | mg/ml | mg/ml | mg/ml |
| SYN3 | 0.001-150 | 0.001-150 | 0.001-150 | 0.001-150 |
| Polysorbate 20 | 0.001-150 | | | |
| Polysorbate 80 | | 0.001-150 | | |
| Pluronic L64 | | | 0.001-100 | |
| Pluronic L92 | | | | 0.001-100 |
| N,N-Dimethylacetamide qs ad | 1 ml | 1 ml | 1 ml | 1 ml |

To prepare, weigh approximately 75% of DMA into a glass beaker. To a separate beaker, charge the surfactant (Polysorbate 80, Polysorbate 20, Pluronic L64 or Pluronic L92) and dissolve in a small volume (approximately 10% of final volume) of DMA. Charge the DMA/surfactant solution into the DMA with constant stirring. Preweigh SYN3 in a separate container. Slowly charge the SYN3 into the solution while stirring. Once the SYN3 is dissolved, add sufficient DMA to final volume by weight (density=0.962 g/ml at 25° C.). Filter the solution through a 0.22 filter attached to a syringe equipped with a nonlatex plunger and store the solution in a tightly sealed glass container at 4° C.

The following Examples may be prepared in accordance with Example 1.

Example 2

| Ingredient | mg/ml |
|---|---|
| SYN3 | 51 |
| Polysorbate 20 | 50 |
| N,N-Dimethylacetamide qs ad | 1 ml |

Example 3

| Ingredient | mg/ml |
|---|---|
| SYN3 | 51 |
| Polysorbate 80 | 50 |
| N,N-Dimethylacetamide qs ad | 1 ml |

Example 4

| Ingredient | mg/ml |
|---|---|
| SYN3 | 51 |
| Pluronic L64 | 25 |
| N,N-Dimethylacetamide qs ad | 1 ml |

Example 5

| Ingredient | mg/ml |
|---|---|
| SYN3 | 51 |
| Pluronic L92 | 25 |
| N,N-Dimethylacetamide qs ad | 1 ml |

The following 25 ml batches were prepared according to the same procedure.

Example 6

| Ingredient | mg/ml |
|---|---|
| SYN3 | 1.275 |
| Polysorbate 20 | 1.250 |
| N,N-Dimethylacetamide qs ad | 25 ml |

Example 7

| Ingredient | mg/ml |
|---|---|
| SYN3 | 1.275 |
| Polysorbate 80 | 1.250 |
| N,N-Dimethylacetamide qs ad | 25 ml |

Example 8

| Ingredient | mg/ml |
|---|---|
| SYN3 | 1.275 |
| Pluronic L64 | 0.625 |
| N,N-Dimethylacetamide qs ad | 25 ml |

Example 9

| Ingredient | mg/ml |
|---|---|
| SYN3 | 1.275 |
| Pluronic L92 | 0.625 |
| N,N-Dimethylacetamide qs ad | 25 ml |

The following is a stability analysis of Examples 2, 3, 4, and 5.

Example 10

| | | T° | | | | |
|---|---|---|---|---|---|---|
| | | −20° C. | 4° C. | 25° C. | 55° C. | −80° C. |
| Ex. No. 2 | 1 week | 52.22 | 52.15 | 52.38 | 51.36 | 52.31 |
| | 2 week | 52.16 | 52.14 | 52.38 | 52.68 | |
| | 3 week | 51.92 | 52.38 | 51.98 | 51.46 | |
| | 4 week | 52.1 | 52.63 | 52.28 | 51.15 | |
| Ex. No. 3 | 1 week | 51.9 | 53.75 | 53.09 | 52.98 | 53.33 |
| | 2 week | 53.46 | 52.9 | 51.98 | 51.75 | |
| | 3 week | 52.64 | 53.35 | 53.41 | 50.6 | |
| | 4 week | 53.41 | 52.96 | 53.85 | 55.81 | |
| Ex. No. 4 | 1 week | 51.34 | 53.94 | 53.68 | 53.76 | 53.98 |
| | 2 week | 53.3 | 53.43 | 53.76 | 52.23 | |
| | 3 week | | 53.14 | 52.56 | 52.35 | |
| | 4 week | 53.72 | 53.67 | 54.2 | 53.42 | |
| Ex. No. 5 | 1 week | 52.34 | 52.16 | 52.43 | 51.48 | 52.33 |
| | 2 week | 51.64 | 51.5 | 51.39 | 52.18 | |
| | 3 week | 52.28 | 52.56 | 53.73 | 53.01 | |
| | 4 week | 53.49 | 53.49 | 53.67 | 53.73 | |

Stability testing was accomplished by HPLC. Solution formulations were placed in the indicated temperature conditions, incubated for specified times and concentrations were determined by HPLC and compared to initial concentrations (−80° C.). The nonaqueous, solution formulations of SYN3 remain stable for at least 1 month at 55° C. when SYN3 is dissolved in N,N-Dimethylacetamide (DMA).

Example 11

The following table represents ranges of the ingredients for lyophilized formulations of the present invention. The compounded solution is filled as indicated into a 20-ml capacity Type II glass vial and lyophilized. Preparation for administration requires addition of 20 ml of WFI to the vial containing the freeze-dried cake to redissolve the SYN3. The SYN3 solution is combined with p53, or any recombinant adenovirus preparation, in a v/v ratio of 1:5. The admixture is then administered to the patient for, for instance, bladder cancer.

| | Range of Concentrations | | |
|---|---|---|---|
| INGREDIENT | mg/ml | mg/ml | mg/ml |
| SYN3 | 0.001-150 | 0.001-150 | 0.001-150 |
| Citric Acid Monohydrate | 0.016-0.72 | 0.016-0.96 | 0.005-1.35 |
| Sodium Citrate Dihydrate | 0.05-2.31 | 0.05-3 | 0.02-5.37 |
| Hydroxypropyl-β-cyclodextrin | — | 50-500 | — |
| BigCHAP | 20-360 | — | — |
| Glycine | 10-200 | — | — |
| Mannitol | — | — | 5-100 |
| Polysorbate 80 | — | 1.0-36.0 | 10-200 |
| Ascorbic Acid[a] | 0.001-0.6 | 0.001-0.6 | — |
| Water for Injection (WFI) qs ad | 1 ml | 1 ml | 1 ml |
| PH Range | 5-6 | 5-6 | 5-6 |
| ml Fill into 20-ml vial[b] | 5.3 | 5.3 | 5.3 |
| Reconstitution Volume of WFI[c] | 20 ml | 20 ml | 20 ml |

The following examples are methods of preparing the lyophilized formulations.

Example 12

| Ingredient | Grams/Liter |
|---|---|
| SYN3 | 24 |
| Citric Acid Monohydrate USP | 0.24 |
| Sodium Citrate Dihydrate USP | 0.77 |
| Big CHAP | 120 |
| Glycine USP | 50 |
| Ascorbic Acid USP | 0.25 |
| Water for Injection USP qs ad | 1000 ml |

The actual amount of SYN3 to be charged will be adjusted according to the purity of the drug substance batch using the following formula:

grams SYN3=24.0×100/(% Purity).

For example:
SYN3 drug substance=97.0% pure.
24.0×100/97.0=24.7 grams SYN3 to be charged for a 1-Liter batch.

Accordingly, to determine the amount of SYN3 that will be charged to the batch according to the following formula:

g SYN3/Liter=24.0 g/Liter×[100/(% SYN3 Batch Purity)]

The volume of Water for Injection to be charged to the batch is to be determined according to the following formula:

Volume of Water for Injection(Liters)=Batch Volume (Liters)×0.5

Charge the volume of water for injection calculated using the formula above into a tared compounding vessel equipped with an agitator. Charge and dissolve, with agitation, the BigCHAP. Sterile Water for Injection may be used to rinse the weighing vessel to retrieve all of the material. Complete dissolution of BigCHAP may require approximately 30 to 60 minutes of continuous agitation at a moderate stirring rate. Charge and dissolve with agitation (moderate stirring rate) the SYN3 into the BigCHAP solution. Water for Injection may be used to rinse the weighing vessel to retrieve all of the material. Complete dissolution of SYN3 may require up to 1 hour of mixing. Charge and dissolve with agitation and in order: Glycine, Ascorbic Acid, Citric Acid Monohydrate and Sodium Citrate Dihydrate into the solution that contains both Big CHAP and SYN3. Water for Injection may be used to rinse the weighing vessels to retrieve all of the material. Add Water for Injection to bring the batch to the final volume (density of the solution is approximately 1.051 g/ml at 25° C.). Mix the solution for a minimum of 15 minutes.

Remove a small (<5 ml) sample of the solution for pH measurement. The pH should be between 5.0 and 6.0. No pH adjustment is necessary. One of ordinary skill in the art can readily ascertain the pH of the resulting product.

To complete compounding, aseptically filter the solution. If necessary, the compounded batch may be stored at 2° C. to 8° C. for up to 24 hours in a sealed, sterilized, stainless steel pressure vessel prior to filling into the vials. The batch may be filtered more than once to assure sterility.

Aseptically fill 5.3±0.1 ml of solution into 20-ml Type 1 flint glass vials that have been washed and sterilized. Aseptically insert 20-mm West 4416/50 lyo-shape rubber stoppers that have been washed, siliconized and sterilized into the vials in the lyophilization position.

Precool the lyophilizer shelves to 4±2° C. Aseptically load the trays of filled vials onto the lyophilizer shelves. After all the trays are loaded, cool the shelves to −40° C. in 1 hour and maintain the product at −35° C. or below for at least 4 hours before proceeding. Start cooling the condenser. When the condenser temperature is at −45° C. or below, begin evacuating the chamber. When 50-70 mm Hg of vacuum pressure is attained, heat the shelf temperature to −20° C. over 0.5 hour. Maintain the shelf temperature at −20° C. for 36 hours at approximately 150 mm Hg pressure (100 to 200 mm Hg pressure). Product temperature must remain at or above −20° C. for at least 6 hours before proceeding. Heat the shelf to 25° C. in 1 hour and reduce pressure to approximately 50 mm Hg pressure. Maintain the shelf temperature at 25° C. at approximately 50 mm Hg pressure for 14 hours. Vent the chamber with sterile filtered nitrogen to approximately 950 mm Hg. Stopper the vials inside the lyophilizer. Remove the vials from the lyophilizer and crimp the vials with 20-mm aluminum seals. The vials should be stored at 2° C. to 8° C. until inspection is completed.

The product is a white to off-white cake. The vials should be stored between 2° C. to 8° C. after inspection. For labeling and inspection purposes, the vials may be exposed to 19° C.-25° C. for up to 6 hours.

The following examples were prepared in accordance with the batch preparation as set forth in Example 12 above.

Example 13

| Ingredient | mg/ml |
|---|---|
| SYN3 | 24 |
| Citric Acid Monohydrate USP | 0.24 |
| Sodium Citrate Dihydrate USP | 0.77 |
| Big CHAP | 120 |
| Glycine USP | 50 |
| Ascorbic Acid USP | 0.25 |
| Water for Injection USP qs ad | 1 Ml |

The pH of the resulting product was 5.34.

| Ingredient | mg/ml |
|---|---|
| SYN3 | 24 |
| Citric Acid Monohydrate USP | 0.32 |

-continued

| Ingredient | mg/ml |
| --- | --- |
| Sodium Citrate Dihydrate USP | 1.02 |
| HPβCD | 200 |
| Polysorbate 80 | 12 |
| Ascorbic Acid USP | 0.25 |
| Water for Injection USP qs ad | 1 ml |

The pH of the resulting product was 5.45.

Example 15

| Ingredient | mg/ml |
| --- | --- |
| SYN3 | 24. |
| Citric Acid Monohydrate USP | 0.45 |
| Sodium Citrate Dihydrate USP | 1.79 |
| Mannitol | 30 |
| Polysorbate 80 | 72 |
| Water for Injection USP qs ad | 1000 ml |

The pH of the resulting product was 5.76.

Stability testing of the resultant lyophilized products of Examples 13, 14 and 15 yielded the following results:

Example 16

| | EXAMPLES | | |
| --- | --- | --- | --- |
| CONDITION | 13 mg/ml | 14 mg/ml | 15 mg/ml |
| Initial | 6.05 | 5.89 | 6.06 |
| 2 weeks −20° C. | 6.02 | 6.04 | 6.28 |
| 2 weeks 4° C. | 6.17 | 5.98 | 6.17 |
| 2 weeks 25° C. | 6.14 | 5.91 | 6.62 |
| 2 weeks 40° C. | 5.87 | 5.78 | 6.32 |
| 4 weeks −20° C. | 6.81 | 5.71 | 6.11 |
| 4 weeks 4° C. | 6.75 | 6.63 | 6.75 |
| 4 weeks 25° C. | 6.81 | 6.40 | 6.92 |
| 4 weeks 40° C. | 6.73 | 6.66 | 6.58 |
| 12 weeks 4° C. | 6.74 | 6.66 | 6.74 |
| 12 weeks 25° C. | 6.74 | 6.45 | 6.72 |
| 12 weeks 40° C. | 6.61 | 6.52 | 6.71 |

Stability testing was accomplished by HPLC. Lyophilized formulations were reconstituted (redissolved) with 19.5 ml WFI. Samples were placed in the indicated temperature conditions, incubated for specified times and concentrations were determined by HPLC and compared to initial concentrations.

Example 17

| Ingredient | mg/ml |
| --- | --- |
| SYN3 | 24.0 |
| Citric Acid Monohydrate USP | 0.32 |
| Sodium Citrate Dihydrate USP | 1.02 |
| Hydroxypropyl-β-cyclodextrin | 200 |
| Polysorbate 80 | 12.0 |
| Ascorbic Acid USP | 0.25 |
| Water for Injection USP qs ad | 1000 ml |

The actual amount of SYN3 to be charged will be adjusted according to the purity of the drug substance batch using the following formula:

grams SYN3=24.0×100/(% Purity).

Sample Calculation:

SYN3 drug substance=97.0% pure.

24.0×100/97.0=24.7 grams SYN3 to be charged for a 1-Liter batch.

The following Example was prepared as such: Initially, determine the amount of SYN3 that will be charged to the batch according to the following formula:

g SYN3/Liter=24.0 g/Liter×[100/(% SYN3 Batch Purity)]

Next, determine the volume of Water for Injection to be charged to the batch according to the following formula:

Volume of Water for Injection(Liters)=Batch Volume (Liters)×0.5

Charge the volume of Water for Injection into a tared compounding vessel equipped with an agitator. Charge and dissolve, with agitation, the Hydroxypropyl-β-cyclodextrin. Note, complete dissolution of Hydroxypropyl-β-cyclodextrin may require approximately 30 to 45 minutes of continuous agitation at a moderate stirring speed. Water for Injection may be used to rinse weighing vessel to retrieve all of the material. Charge and dissolve the Polysorbate 80 to the solution. The Polysorbate 80 may be predissolved in 0.1×total batch volume of Water for Injection (Liters) and charged to the solution.

Charge and dissolve with agitation the SYN3 into the solution. Complete dissolution of SYN3 may require up to 1 hour of mixing. Water for Injection may be used to rinse weighing vessel to retrieve all of the material.

Charge and dissolve with agitation and in order: Ascorbic Acid, Citric Acid monohydrate and Sodium Citrate dihydrate into the solution. Water for Injection may be used to rinse weighing vessels to retrieve all of the material. Add the Water for Injection to bring the batch to the final volume (density of solution is 1.058 g/ml at 25° C.). Mix the solution for a minimum of 15 minutes.

Remove a small (<5 ml) sample of the solution for pH measurement. The pH should be between 5.0 and 6.0. No pH adjustment is necessary. Aseptically filter the solution that has been washed and tested for integrity into a sterilized, stainless steel pressure vessel or equivalent should be used. If necessary, the compounded batch may be stored at 2° C. to 8° C. for up to 24 hours in a sealed, sterilized, stainless steel pressure vessel prior to filling. The batch may be filtered more than once to assure sterility.

Aseptically fill 5.3±0.1 ml of solution into 20-ml Type 1 flint glass vials that have been washed and sterilized. Aseptically insert lyo-shape rubber that have been washed, siliconized and sterilized into the vials in the lyophilization position.

To lyophilize, precool the lyophilizer shelves to 4±2° C. Aseptically load the trays of filled vials onto the lyophilizer shelves. After all the trays are loaded, cool the shelves to −40° C. in 1 hour and maintain the product at −35° C. or below for at least 4 hours before proceeding. Start cooling the condenser. When the condenser temperature is at −45° C. or below, begin evacuating the chamber. When 50-70 mm Hg of vacuum pressure is attained, heat the shelf temperature to −20° C. over 0.5 hour. Maintain the shelf temperature at −20° C. for 36 hours at approximately 150 mm Hg pressure (100 to 200 mm Hg pressure). Product temperature must remain at or above −20° C. for at least 6 hours before proceeding. Heat the shelf to 25° C. in 1 hour and reduce pressure to approximately 50 mm Hg pressure. Maintain the shelf temperature at 25° C. at approximately 50 mm Hg pressure for 14 hours. Vent the chamber with sterile filtered nitrogen to approximately 950 mm Hg. Stopper the vials inside the lyophilizer. Remove the vials from the lyophilizer and crimp the vials with 20-mm aluminum. The vials should be stored at 2° C. to 8° C. until inspection is completed.

The product is a white to off-white cake. The vials should be stored between 2° C. to 8° C. after inspection. For labeling and inspection purposes, the vials may be exposed to 19° C.-25° C. for up to 6 hours.

p53 (rAD/p53) remains stable when combined with the lyophilized formulations of SYN3 for at least 2 hours at 37° C. and 24 hours at 25° C. p53 remains stable when combined with the aqueous solution formulations of SYN3 for at least 4 hours at 37° C. and 24 hours at 25° C.

Example 18

Figure 2:
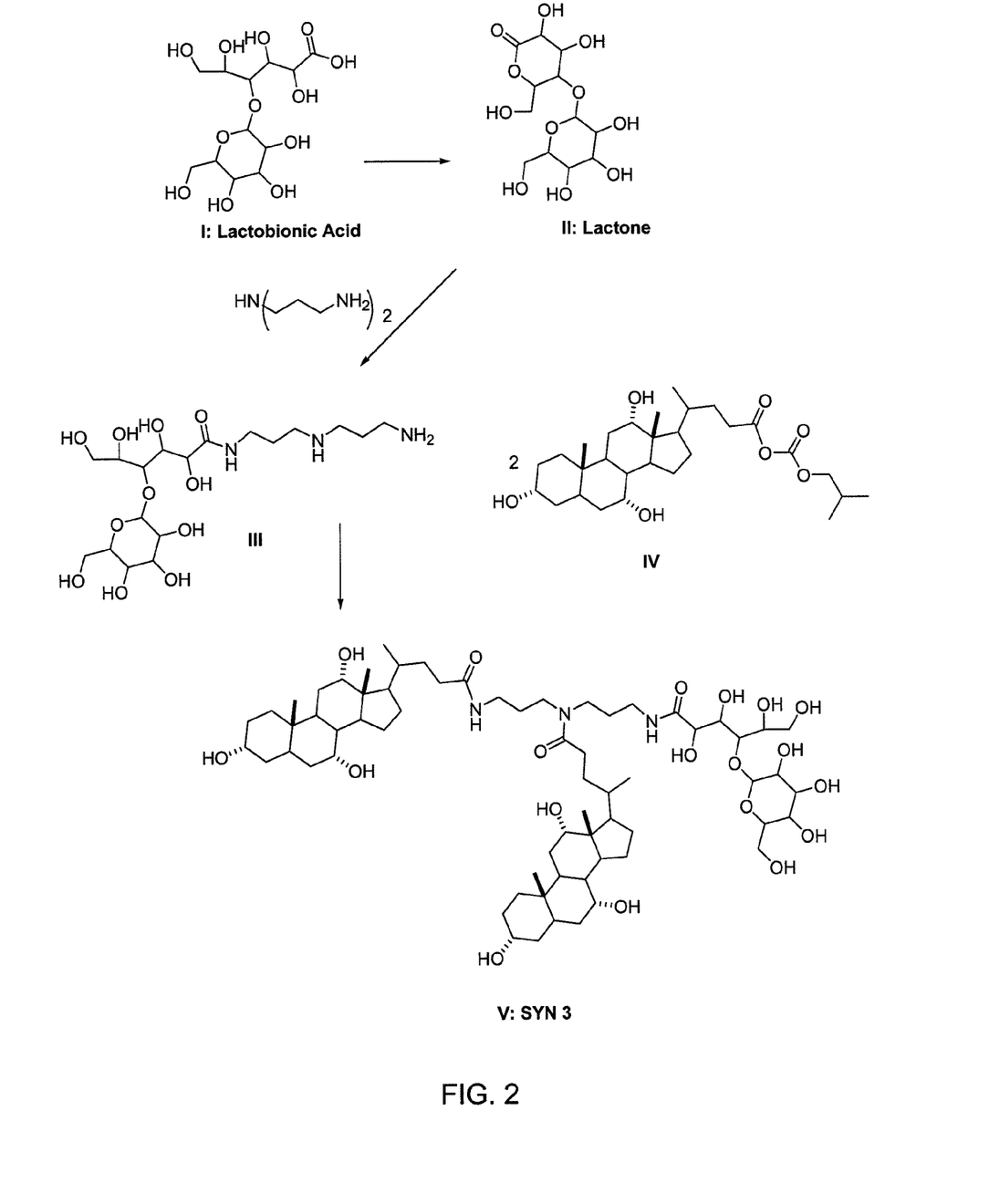
FIG. 2 illustrates one method for the synthesis of SYN3.

This example illustrates the synthesis of SYN3.
Part 1: Synthesis of Compound III
The synthetic scheme for SYN3 is shown in FIG. 2, which is adapted from U.S. Pat. No. 6,392,069. The lactone of lactobionic acid (II) was synthesized by dissolving one g (2.8 mmol) of lactobionic acid (I) in 50 ml of methanol, evaporating to dryness on a rotary evaporator, and repeating this process six times. To obtain Compound III, the resulting residue (II) was dissolved in 50 ml of isopropanol by heating to 50° C. To this solution was added 1.2 ml (8.4 mmol) of N-3-aminopropyl)-1,2-propanediamene. The temperature was increased to 100° C., and the solution was stirred for three hours. The solvent was removed by rotary evaporation and the resulting residue was washed several times with chloroform to remove excess unreacted N-(3-aminopropyl)-1,3-propanediamene. The remaining residue (III) was used as is in Part 3 below.
Part 2: Synthesis of Compound IV
Compound IV was synthesized by dissolving 2.28 g of cholic acid (5.6 mmol) in N,N-dimethylformamide by heating to 60° C. Triethylamine (0.78 ml (5.6 mmol)) was added and the solution was cooled in an ice bath. Isobutyl chloroformate (0.73 ml (5.6 mmol)) was then added and a white precipitate formed as the stirring was continued for ten minutes.
Part 3: Synthesis of SYN3 (Compound V)
Compound III was dissolved in N,N-dimethylformamide, cooled in an ice bath, and stirred. The suspension resulting from the synthesis of Compound IV was filtered into the solution containing Compound III. The resulting solution was stirred at room temperature for 6 hrs. The solvent was removed using high vacuum rotary evaporation and the residue was dissolved in 100 ml of chloroform/methanol (50/50). Twenty-five ml of this solution was purified by silica gel flash chromatography using chloroform/methanol (60/40) as the elution solvent. Analysis of the fractions eluting from the column was conducted by silica gel thin layer chromatography using a mobile phase consisting of chloroform/methanol/water/concentrated ammonium hydroxide (100/80/10/5). The compounds were visualized by charring after spraying with ethanolic sulfuric acid. Fractions containing product were consolidated and repurified using flash chromatography and chloroform/methanol/water/concentrated ammonium hydroxide (100/80/10/5) as the elution solvent. Fractions containing product were consolidated and evaporated to a white powder (300 mg of Compound V). $^1$H-NMR and MALDI mass spectrometric analysis of the product were consistent with the structure shown.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the Examples contained in the foregoing description.

It is understood that the examples and embodiments described herein are for illustrative purposes only and that various modifications or changes in light thereof will be suggested to persons skilled in the art and are to be included within the spirit and purview of this application and scope of the appended claims. All publications and patent applications cited in this specification are herein incorporated by reference in their entirety for all purposes as if each individual publication or patent application were specifically and individually indicated to be incorporated by reference.

What is claimed is:

1. A method of treating a bladder cancer in a mammal, said method comprising:
  intravesically administering to the urinary bladder of the mammal a therapeutically effective amount of a pharmaceutical composition comprising SYN3, hydroxypropyl-beta-cyclodextrin, a polysorbate, a citrate buffer, and a recombinant viral vector encoding an interferon α, thereby treating the bladder cancer in the mammal; wherein just prior to administration to the mammal, the pharmaceutical composition is prepared by
  a) reconstituting in water a lyophilized formulation lacking the vector and comprising the SYN3, the hydroxypropyl-beta-cyclodextrin, the polysorbate, and the citrate buffer, wherein the formulation has a pH ranging from 5 to 6 prior to the lyophilization, thereby forming a reconstituted SYN3 formulation, and;
  b) mixing the reconstituted SYN3 formulation with the recombinant viral vector.

2. The method of claim 1, wherein said polysorbate is selected from Polysorbate 80 and Polysorbate 20.

3. The method of claim 2, wherein the reconstituted SYN3 formulation comprises the Polysorbate 80 in a concentration of 1 to 36 mg/ml, and the hydroxypropyl-beta-cyclodextrin in a concentration of 50 to 500 mg/ml.

4. The method of claim 1, wherein the interferon α is interferon α2b.

5. The method of claim 1, wherein the recombinant viral vector is a recombinant adenoviral vector.

6. The method of claim 1, wherein the mixing forms an admixture with a pH from about 7 to 8.5.

7. The method of claim 1, wherein the mixing forms an admixture with a pH of about 7.4.

* * * * *